United States Patent
Seidenberg et al.

(10) Patent No.: US 9,339,573 B2
(45) Date of Patent: May 17, 2016

(54) APPARATUS AND METHOD FOR THE EXTERNAL STERILIZATION OF PLASTICS MATERIAL PRE-FORMS

(71) Applicant: KRONES AG, Neutraubling (DE)

(72) Inventors: Katharina Seidenberg, Karlsruhe (DE); Bettina Kohl, Ensdorf (DE); Michael Loy, Regensburg (DE); Juergen Soellner, Beratzhausen (DE); Marina Goldbach, Bad Abbach (DE); Robert Schmitt, Schierling (DE); Ute Bedoe, Ergoldsbach (DE)

(73) Assignee: KRONES AG, Neutraubling (DE)

( * ) Notice: Subject to any disclaimer, the term of this patent is extended or adjusted under 35 U.S.C. 154(b) by 80 days.

(21) Appl. No.: 14/221,088

(22) Filed: Mar. 20, 2014

(65) Prior Publication Data
US 2014/0322074 A1    Oct. 30, 2014

(30) Foreign Application Priority Data

Apr. 24, 2013  (DE) .......................... 10 2013 104 152

(51) Int. Cl.
*A61L 9/00* (2006.01)
*A61L 2/00* (2006.01)
*B08B 9/04* (2006.01)
(Continued)

(52) U.S. Cl.
CPC ... *A61L 2/16* (2013.01); *A61L 2/00* (2013.01); *A61L 9/00* (2013.01); *B29C 49/4252* (2013.01); *B29C 49/06* (2013.01); *B29C 49/4205* (2013.01); *B29L 2031/16* (2013.01)

(58) Field of Classification Search
CPC ............ A61L 2/00; B08B 9/00; B67C 7/0073
USPC ......... 422/1, 28, 32, 292, 297–298, 300, 307; 134/8, 22.1, 23–24, 25.1, 32, 48
See application file for complete search history.

(56) References Cited

U.S. PATENT DOCUMENTS

| | | | |
|---|---|---|---|
| 2005/0118057 A1 | 6/2005 | Quetel |
| 2008/0152538 A1 | 6/2008 | Quetel |

(Continued)

FOREIGN PATENT DOCUMENTS

| | | |
|---|---|---|
| CN | 101219229 A | 7/2008 |
| CN | 102209560 A | 10/2011 |

(Continued)

OTHER PUBLICATIONS

European Search Report; EP14001461, Dated Aug. 18, 2014.

(Continued)

*Primary Examiner* — Monzer R Chorbaji
(74) *Attorney, Agent, or Firm* — Oppedahl Patent Law Firm LLC

(57) ABSTRACT

An apparatus (1) for the sterilization of plastics material containers (10), and in particular of plastics material pre-forms (10), with a conveying device (2) which conveys the plastics material containers (10) along a pre-set conveying path, with at least one stressing device (4) which acts upon an external surface of the plastics material containers to be sterilized with a flowable medium. According to the invention the stressing device is arranged in such a way that it acts upon a pre-set area of the plastics material containers (10)—situated below an aperture of the plastics material pre-forms—with the sterilization medium.

18 Claims, 3 Drawing Sheets

(51) Int. Cl.
  B08B 9/00 (2006.01)
  B08B 1/02 (2006.01)
  B08B 3/00 (2006.01)
  A61L 2/16 (2006.01)
  B29L 31/16 (2006.01)
  B29C 49/06 (2006.01)
  B29C 49/42 (2006.01)

(56) References Cited

U.S. PATENT DOCUMENTS

| | | | |
|---|---|---|---|
| 2009/0229795 A1 | 9/2009 | Takatomi | |
| 2010/0199604 A1* | 8/2010 | Fischer | B67C 7/0073 53/425 |
| 2011/0061343 A1 | 3/2011 | Roithmeier | |
| 2011/0272861 A1 | 11/2011 | Humele | |

FOREIGN PATENT DOCUMENTS

| | | |
|---|---|---|
| CN | 102282093 A | 12/2011 |
| DE | 19956186 | 5/2001 |
| DE | 60306349 | 6/2007 |
| DE | 102009041215 | 3/2011 |
| EP | 1941913 A1 | 7/2008 |
| EP | 2394950 | 12/2011 |
| EP | 2394950 A | 12/2011 |
| JP | 2009274740 | 11/2009 |
| WO | 2008/049876 A1 | 5/2008 |

OTHER PUBLICATIONS

China Patent Office Action 518040 dated Nov. 27, 2015.
English translation of the above from Global Dossier.

* cited by examiner

APPARATUS AND METHOD FOR THE EXTERNAL STERILIZATION OF PLASTICS MATERIAL PRE-FORMS

The present invention relates to an apparatus and a method for the external sterilization of plastics material containers, and in particular of plastics material pre-forms. In order to improve the shelf life of filled products—in particular sensitive filled products—in plastics material containers, such as for example PET bottles, to a decisive degree it is known to reduce the number of the germs in the containers to a significant extent before the filling process. To this end, different wet and dry aseptic methods are known in the prior art and in the field of filling technology. In this case it is known for example for a sterilization medium such as hydrogen peroxide or peracetic acid to be introduced into the interior of the plastics material containers. In addition, methods are known in which electron beam emitters are introduced into the interior of the plastics material containers. The invention is described here with reference to plastics material containers, but it is pointed out that an application to other containers such as for example glass containers is also possible.

On account of the in part large volumes of containers of this type, however, a high degree of consumption of the sterilization media occurs when the latter are used.

Apparatus and methods are therefore known from the prior art which do not sterilize the already shaped containers but the plastics material pre-forms which are then shaped to form the plastics material containers. In other words the number of the germs is already reduced inside the plastics material pre-form (also referred to as pre-form below) before the blow moulding of the containers. In this case this plastics material pre-form passes through a treatment area in which the disinfection is achieved by gaseous or liquid sterilization media or by irradiation (UV, electron beam and the like).

After this disinfection procedure, recontamination should advantageously be prevented until the filled container is closed. To this end, the shaping procedure of the plastics material pre-forms is ideally carried out under sterile conditions. In order to maintain the sterile conditions there during the production, no germs should be conveyed into the sterile area by the plastics material pre-forms. They could be deposited there and subsequently reach a following pre-form.

The object of the present invention is therefore to disinfect, in particular, as well as the internal faces, also the external faces of the plastics material pre-forms. This object is attained according to the invention by the subjects of the independent claims. Advantageous embodiments and further developments form the subject matter of the sub-claims.

An apparatus according to the invention for the sterilization of plastics material containers, and in particular plastics material pre-forms, has a conveying device which conveys the plastics material containers along a pre-set conveying path. In addition, the apparatus has at least one acting upon device (below also referred to as "stressing device") which acts upon an external surface of the plastics material containers to be sterilized with a flowable (in particular a gaseous and/or liquid) medium.

According to the invention the stressing device is arranged in such a way that it acts upon a pre-set area of the plastics material containers—situated below an aperture of the plastics material pre-form—with the sterilization medium.

The Applicants have discovered that within the framework of sterilization procedures of this type a particularly critical area is just the external face of the plastics material pre-forms, since the germs present there are situated in the immediate vicinity of the internal surface. As a result, there is a relatively high risk of these germs being able to reach the pre-form or container respectively and/or subsequent pre-forms during the process steps following the disinfection. Contrary to earlier assumptions, particular importance is therefore attached to the disinfection of the external surfaces of the plastics material pre-form. In the case of a plant which became known to the Applicants from the internal prior art, a disinfection action is achieved by the plastics material pre-forms being conveyed during the internal disinfection through a treatment area in the surroundings of which an increased concentration of the sterilization medium is present. In the case of sensitive filling products, such as for example weakly acidic beverages, however, the disinfection rates achieved in this way on the external faces have been found to be inadequate.

In the preferred embodiments described below, therefore, possibilities for achieving an improved disinfection of the external faces will also be described.

In the case of a preferred embodiment the sterilization medium is a gaseous medium, for example hydrogen peroxide or peracetic acid. It is preferable for the conveying device to convey the plastics material containers, which are in particular plastics material pre-forms, in a horizontal plane. It is preferable for the conveying device to convey the plastics material pre-forms along a circular conveying path. In the case of a further advantageous embodiment the apparatus has a further sterilization device which also sterilizes the internal surfaces of the plastics material pre-forms. This can be both an apparatus which acts upon these internal surfaces of the plastics material pre-forms with the sterilization medium, but it would also be possible for this further sterilization device to act upon the internal surfaces of the plastics material pre-forms with radiation, in particular UV or electron radiation.

In the case of a further advantageous embodiment the apparatus has a shaping device which shapes plastics material pre-forms into plastics material containers. It is advantageous for this shaping device to have a clean room or sterile room respectively, inside which the plastics material pre-forms are shaped into the plastics material containers. In this case this shaping device preferably also has a stressing device which acts upon the plastics material pre-forms with a gaseous medium, and in particular acts upon them with sterile air, for the purpose of their expansion.

In the case of a further advantageous embodiment the apparatus also has a heating device which heats the plastics material pre-forms. The sterilization devices described here are preferably arranged downstream with respect to the heating device in the conveying direction of the plastics material pre-forms, i.e. in particular between the heating device and the shaping device. It would also be possible, however, for the external and/or internal sterilization of the plastics material pre-forms to be carried out before the heating and even for the heating device to have a clean room or sterile room respectively, through which the plastics material pre-forms are conveyed during the heating thereof. In addition, the (pre-)sterilization of the plastics material pre-forms inside the heating device would be possible.

In the case of a further advantageous embodiment the stressing device or at least one stressing device is arranged below the conveying path of the plastics material pre-forms. This should be understood as being that the stressing device is preferably arranged below a base portion of the plastics material pre-forms or below a plane above which the plastics material pre-forms are conveyed. It is pointed out that apparatus in which the plastics material pre-forms are conveyed with the apertures thereof downwards are also known from the prior art. In this case the stressing device is arranged accordingly in such a way that it acts upon a pre-set area of the plastics material pre-forms—situated above the apertures of the plastics material pre-forms—with the sterilization medium.

The term "below" is therefore understood as being the situation in which the plastics material pre-form is arranged standing upright with the aperture upwards. In addition, the conveying plane of the plastics material pre-forms can also be understood as being that plane which is defined by the aperture of the plastics material pre-forms or the upper aperture edge of the plastics material pre-forms respectively. In this way, with this design it is proposed that at least one outlet opening of the stressing device, through which the sterilization medium arrives at the plastics material pre-forms, should be situated below the conveying path or at least below a vertical level of an aperture portion of the plastics material pre-forms. It is pointed out that it would also be possible in this case for the stressing devices to be arranged in part or even completely above this level, for example if deflecting devices are provided which direct the sterilization medium (exclusively) to an area below the aperture and/or a carrying ring of the plastics material pre-forms.

It is advantageous for the stressing devices to be arranged below the conveyed plastics material pre-forms. In this way, in particular, a base region of the plastics material pre-forms is also acted upon with the sterilization medium. It would also be possible, however, for the stressing devices to be arranged laterally adjacent to the conveying path of the plastics material containers.

It is advantageous for at least one stressing device to be arranged in such a way that sterilization medium issuing therefrom flows at least in part in a direction which also has a component which extends from the base region of the plastics material pre-forms to the aperture region thereof in the longitudinal direction thereof.

In the case of a further advantageous embodiment at least one stressing device of the apparatus is vertically adjustable (with respect to the containers), i.e. the relative position of at least one stressing device can be altered relative to the containers in a longitudinal direction thereof. In this case it would be possible and preferred for a position of the stressing devices to be altered, but a change in the position of the containers would also be possible. In this way, an adaptation to different heights or geometries respectively of the plastics material pre-forms to be sterilized can be made possible.

In the case of a further advantageous embodiment the apparatus has a plurality of stressing devices. These can be arranged in this case on a common carrier. In this case it is possible for example for an annular duct to supply the sterilization medium to the individual stressing devices and for the latter then to act upon the plastics material pre-forms.

In the case of a further advantageous embodiment the apparatus has a first wall which extends in a direction of the conveying path and which is preferably situated at the side of the conveying path. With a possibility of release in order to increase the concentration of the gaseous sterilization medium—in particular in the immediate surroundings of the external surface of the plastics material pre-form—it is therefore proposed that the treatment area for the plastics material pre-forms or the treatment area around the conveying path of the plastics material pre-forms respectively should be reduced. To this end, it is possible for example for this conveying path to be bounded by the wall described here. In general it would be advantageous for the conveying path to be enclosed completely or in part by walls, such as for example bent baffle plates. In this case it is possible for these walls to be attached around the conveying path on the outside or the inside or for example also in a U shape with respect to the conveying path.

It is preferred for the apparatus therefore to have a second wall, in which case the conveying path of the plastics material pre-forms is arranged between the first wall and the second wall. It is preferred for the apparatus therefore to have a duct, inside which the plastics material pre-forms are conveyed and inside which they are preferably also acted upon with the flowable sterilization medium.

In the case of a further advantageous embodiment the apparatus has a plurality of stressing devices which are arranged one behind the other along the conveying path of the plastics material containers. In this way, it is also possible for a plurality of stressing devices to be acted upon on their external surface substantially at the same time with the sterilization medium. In this case it is possible for these stressing devices to be arranged so as to be stationary. It would also be possible, however, for these stressing devices to be jointly moved with the plastics material pre-forms or also to be moved for example in a direction opposed to the conveying direction of the plastics material pre-forms.

In the case of a further advantageous embodiment the apparatus has a flow generation device which generates a flow of the flowable medium in the region of the conveying path. This can be for example an active device, such as for example a ventilation device which generates a flow on the external surface of the plastics material pre-forms. In particular, a flow (in particular turbulent) of the sterilization medium should be generated in this way in the surroundings of the plastics material pre-forms.

In the case of this procedure it is therefore proposed that the disinfection procedure should be improved by the conveying of substances being improved by a purposeful flow around the external surfaces to be disinfected. This flow can be effected for example by a fan which is situated in the treatment area and which is orientated in the direction of the conveying path of the plastics material pre-forms. In addition, a suitable blower could also be used. The fan or the blower respectively can have in this case a separate drive which is preferably situated outside the treatment area. As an alternative or in addition, it would also be possible for the driving power to branch off from the rotational movement of the conveying star wheels or the conveying device respectively by way of a suitable gear mechanism.

In addition, it would also be possible for the flow around the plastics material pre-forms to be generated with the aid of one or more nozzles. In this case it is possible for the nozzle or the nozzles preferably to have the gaseous sterilization medium flow through it or them. In particular, it is possible in this case for the nozzles in one embodiment to be installed in a fixed manner in the treatment area and to be orientated in the direction of the conveying path of the plastics material pre-forms. In the case of a particular embodiment a plurality of stressing devices or nozzles respectively are arranged in this case at least in part along the conveying path below or at the side of the plastics material pre-forms. In this case it is also possible, in particular in the case of the embodiment of the arrangement below the plastics material pre-forms, for the vertical level of the outlet openings of the stressing devices to be capable of being adapted to the length of the plastics material pre-forms, for example by the vertical adjustment described above, but also optionally by attachments of different length for the stressing devices.

Alternatively, the stressing devices can also be moved jointly with the plastics material pre-form at least in part along the conveying path in the treatment area. In this case it is possible for the stressing devices in turn to be arranged below or at the side of the plastics material pre-form or the conveying path thereof respectively. In addition, in the case of jointly moved stressing devices of this type an adaptation of the vertical level to the position or length respectively of the plastics material pre-forms by a displacement mechanism or various attachment nozzles is possible. In addition, it would also be possible to use individual possibilities of solution in a combined manner, for example the nozzles combined with an enclosing means.

In this way, in the case of a further advantageous embodiment a plurality of stressing devices are arranged on a common ring, for example a nozzle ring. In this case a turbulent flow can be generated for example on the external surface of the plastics material pre-forms outside the laminar boundary layer in order to increase the exchange of substances. In this way, more germs can be destroyed in a shorter time.

In the case of a preferred embodiment possibilities are therefore present which ensure a turbulent flow of the sterilization medium in the surroundings of the plastics material pre-forms. In other words it is preferred for the sterilization medium in the region of the plastics material pre-forms to be turbulent. In this way, an improved disinfection can be made possible in a shorter time. In the case of a variant the stressing devices are arranged on a common carrier and this carrier can be moved in a direction opposed to the conveying direction of the plastics material pre-forms. It is advantageous for this to be a rotatable carrier, so that a carrier of this type can be rotated. In addition, in the case of this preferred embodiment the conveying device for conveying the plastics material pre-forms is preferably a rotatable wheel or has such a wheel. It is therefore preferred in general for means to be provided which promote a turbulence of the sterilization medium in the region of the plastics material pre-forms, namely in particular means which generate a turbulence or increase that turbulence which arises from the mere relative movement of the plastics material pre-forms with respect to the surroundings thereof. In this case it would be possible for example for devices to be provided which allow a change in the flow of the sterilization medium in particular in the region of the plastics material pre-forms as well.

This would have the advantage that a sterilization medium which preferably occurs in a turbulent manner from the stressing device, is actively swirled, since the conveying of the plastics material pre-forms generates a flow in a first direction and the carrier of the stressing device generates a flow in an opposite direction thereto, i.e. in a direction opposed to the first direction. In addition, a rotational speed of the carrying ring for the stressing devices can be adapted or set in such a way that in a manner dependent upon the geometry of the plastics material pre-forms inter alia an optimum turbulent flow is always generated in the surrounding area of the external surface of the plastics material pre-forms, or the presence of a turbulent flow is assisted respectively. As an alternative or in addition, it is also possible for the nozzle ring to be automatically adjusted in the height thereof with reference to the geometry of the plastics material pre-forms in order to influence the flow conditions.

In the case of a further advantageous embodiment the apparatus has a deflecting device which deflects a flow of the flowable sterilization medium. In this case it is possible for example for a pre-set portion of the sterilization medium issuing from the stressing device (also) to arrive at this deflecting device and, in this way, also preferably to be deflected onto an external surface of the plastics material pre-forms. In this case it is possible for a flow deflecting device of this type to be arranged in a fixed manner and to divert the gas flow in such a way that a plastics material pre-form is comprehensively wetted with the sterilization medium. In this case it is possible for a deflecting device of this type to be arranged inside a conveying path of the plastics material pre-forms (in particular in the case of a circular conveying path).

In addition, it is also possible for a deflecting device of this type to be arranged at a pre-set angle (for example with respect to a longitudinal direction of the plastics material pre-forms) and to deflect a jet of the gaseous sterilization medium striking it, in order to achieve a wide wetting of the plastics material pre-form. In addition, it would be possible for a deflecting device of this type to be made angled, for example in such a way that the gas flow of the sterilization medium strikes the plastics material pre-form in a multiple manner.

This deflecting device can be arranged so as to be stationary in this case, but it would also be possible for it to be jointly moved with the stressing devices and/or the plastics material pre-forms to be sterilized.

In the case of a further advantageous embodiment, as described above, a further apparatus for the sterilization of internal surfaces of the plastics material pre-form is provided, this further apparatus preferably being provided in such a way that a simultaneous internal and external sterilization of the plastics material pre-forms is possible, at least for a time.

In this context it should be pointed out that from the physical point of view turbulent flow does not occur on the external surface of the plastics material pre-forms themselves. A laminar flow is always present in a laminar boundary layer around the plastics material pre-forms, since the speed directly on the surface of the plastics material pre-form is zero on account of the fluid friction and then increases as the distance from the surface increases. At a specified distance the so-called critical Reynolds number is exceeded and the flow is then turbulent. A conveying of substances by diffusion then takes place in the immediate surroundings of the external surface and a more rapidly occurring diffusion by the swirling in the flow takes place outside the laminar boundary layer.

In the case of a further advantageous embodiment stressing devices are provided for acting upon the internal surfaces of the plastics material pre-forms, which are preferably designed so as to be movable with the plastics material pre-forms, the stressing devices being arranged in such a way that they inject the flowable medium into the plastics material pre-forms at a pre-set angle different from 0° with respect to a longitudinal direction of the plastics material pre-forms and/or the longitudinal directions of the stressing devices are arranged so as to be offset with respect to the longitudinal direction of the plastics material pre-forms. In this way, an extremely efficient internal sterilization of the plastics material pre-forms is also achieved, since swirling of the sterilization medium or of the flow thereof is also produced in the interior of the plastics material pre-forms.

In this case it is also possible for an injection device of the sterilization medium to have a component which is orientated in a direction opposed to the conveying direction of the plastics material pre-forms.

In the case of a further advantageous embodiment the apparatus has a further sterilization device which sterilizes an internal surface of the plastics material pre-forms. This can be a sterilization device which likewise acts upon the plastics material pre-forms with a flowable medium for their sterilization, but it is also possible to use a sterilization device which acts upon these internal surfaces with radiation, for example with a charge carrier radiation and, in particular, with an electron beam.

The present invention further relates to a method of sterilization of plastics material pre-forms, in which the plastics material pre-forms are conveyed along a pre-set conveying path and at least one region of an external surface of the plastics material pre-forms is acted upon with a flowable (i.e. in particular gaseous and/or liquid) sterilization medium during this conveying. According to the invention at least one region of the external surface of the plastics material pre-forms, which is situated below an aperture region of the plastics material pre-forms, is acted upon by at least one stressing device. In this case "below" is again understood as being that this region is situated between an aperture region and a base region of the plastics material pre-form, "below" being understood in particular with reference to an upright position of the plastics material pre-form (with the aperture upwards). It is therefore advantageous for a base region of the plastics material pre-form also to be acted upon. In this way, it is preferable for an external surface of the container to be acted upon with the sterilization medium.

In the case of a preferred method a flow of the sterilization medium is actively generated in a surrounding region of the plastics material pre-forms. In this case "active" is to be understood as being that this flow is not generated or is generated not only by a movement of the plastics material pre-forms, but further steps are preferably additionally carried out, such as for example a movement of the stressing device, in particular relative to the movement of the plastics material pre-forms and/or an absolute movement of the stressing devices or the use of a blower or the like.

In the case of a further advantageous method the plastics material pre-forms are conveyed during the sterilization through a conveying channel which surrounds the conveying path of the plastics material pre-forms at least locally. It is advantageous in this case for this conveying channel to be formed by at least two walls between which the conveying path of the plastics material pre-forms extends. In addition, a third wall can be provided below the conveying path of the plastics material pre-forms.

In the case of a further advantageous method an internal sterilization of the plastics material pre-forms is also carried out, preferably therefore also an internal surface of the plastics material pre-forms at least locally. As mentioned above, an internal surface can be acted upon for example with a sterilization medium in this case, but it would also be possible, as an alternative or in addition, for this internal surface to be acted upon with radiation for the purpose of sterilization.

It is preferable in this case for this internal sterilization to be carried out at the same time as the external sterilization, at least in part. In this way, it would be possible for the plastics material pre-forms to be sterilized on their external surfaces and their internal surfaces at the same time.

Further advantages and embodiments are evident from the accompanying drawings. In the drawings FIG. 1 is a diagrammatic illustration to explain the invention;

Figure 1:
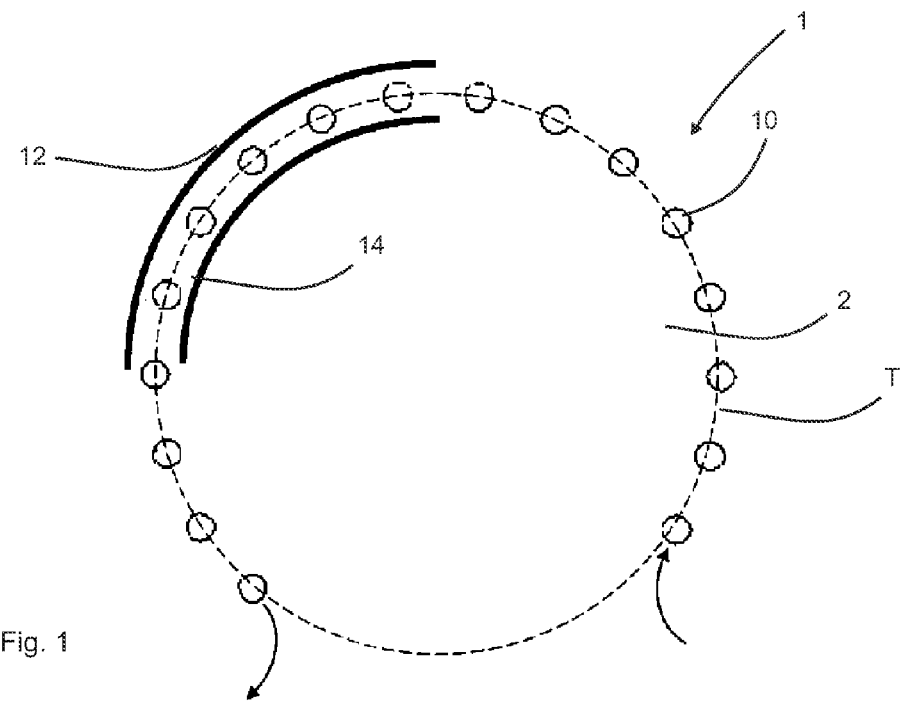

FIG. 1 is a diagrammatic illustration to explain the invention. In this case a rotatable carrier 2, by means of which the plastics material pre-forms 10 are moved along the conveying path T thereof, is illustrated diagrammatically. The two arrows at the bottom indicate a supply of the plastics material pre-forms and a removal of the plastics material pre-forms from the apparatus 1 according to the invention. The rotatable carrier 2 in this case forms the apparatus for the sterilization of the plastics material pre-forms 10 and is preferably arranged downstream of a heating device (not shown) and upstream of a follower machine, such as for example a stretch blow moulding machine (not shown).

The conveying path T extends between two curved walls 12 and 14, the curvatures of which are in turn adapted to the curvature of the conveying path T. In this case these two walls 12, 14 can also cover larger regions of the conveying path T than is shown here in FIG. 1.

Figure 2:
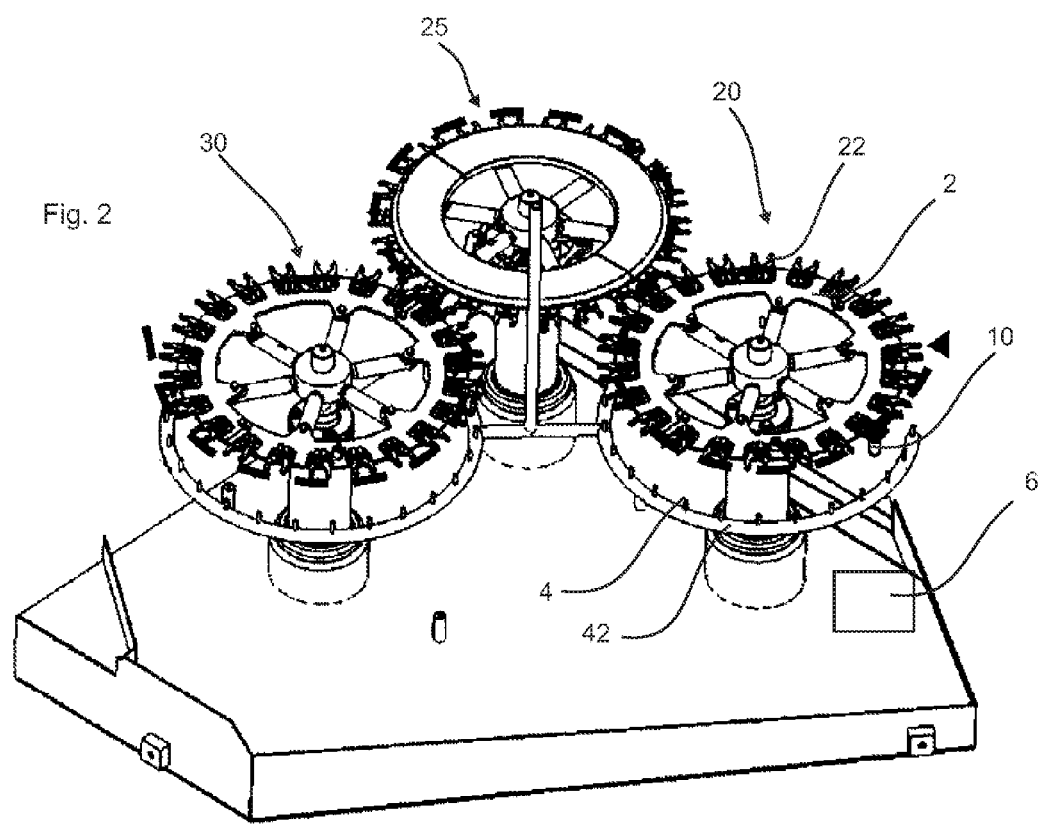
FIG. 2 shows an apparatus according to the invention [in] a first embodiment.

FIG. 2 is a diagrammatic illustration of an apparatus 1 according to the invention. This apparatus has in this case two sterilization units 20 and 30, only the one on the right being provided with reference numerals. These two sterilization units 20, 30 have provided between them a conveying device 25 which conveys the plastics material pre-forms from the first sterilization unit 20 to the second sterilization unit 30.

The rotatable carrier 2, on which a plurality of holding devices 22 for holding the plastics material pre-forms 10 are arranged, is again evident. These holding devices 22 are in this case gripping clamps which engage in the plastics material pre-forms 10 in a region of the aperture thereof. These holding devices can be, in particular, controllable holding devices, i.e. holding devices, the opening state and closing state respectively of which can be controlled.

Only one plastics material pre-form 10, however, is illustrated. The reference number 4 designates a stressing device which is designed in this case in the form of a nozzle. The reference number 42 designates an annular duct which supplies the plurality of stressing devices, which are arranged one behind the other along the conveying path of the plastics material pre-forms 10, with the sterilization medium. In the case of the embodiment shown in FIG. 2 this annular duct 42 is arranged so as to be stationary and the plastics material pre-forms 10 move with respect to it.

The reference number 6 designates in a roughly diagrammatic manner a flow generation device which generates a flow of the sterilization medium. This flow generation device can be for example a blower or the like.

In addition, the apparatus preferably has an enclosure (not shown), so that the plastics material pre-forms are conveyed inside an enclosure. In this case it would be possible for the entire internal space to be designed in the form of a clean room which is sealed off with respect to the environment. In addition, stressing devices can also be present which act upon this clean room with an overpressure as compared with an (in particular atmospheric) external pressure.

It would also, however, be possible for only the conveying path of the plastics material pre-forms to be enclosed in the manner of a duct (not shown). In this case the flow generation device 6 could be arranged for example on or at or in one of the walls which bound the conveying path of the plastics material pre-forms.

Figure 3:
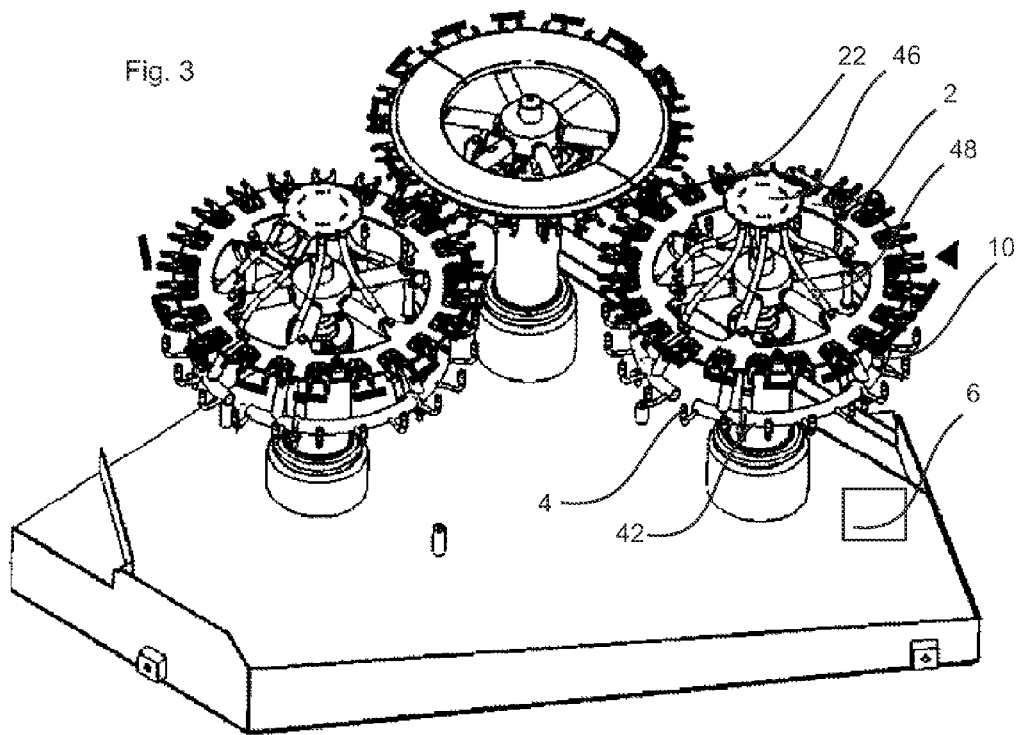
FIG. 3 shows an apparatus according to the invention in a second embodiment.

FIG. 3 shows a further embodiment of the apparatus according to the invention. In the case of this embodiment the individual stressing devices 4 and, in particular, also the annular duct 42 thereof are arranged so as to be rotatable. In this case, as mentioned above, it is possible for the stressing devices to move jointly with the plastics material pre-forms, but also for another rotation, for example in the opposite direction of rotation, to be generated. The reference number 46 designates a distribution device, which distributes the sterilization medium to the duct or the individual stressing devices respectively. To this end, a plurality of lines 48 can be provided which convey the sterilization medium to the stressing devices 4. In addition, the flow generation device 6 can also be provided again here. An internal disinfection can also be carried out parallel or even (at least in part) offset in time or place from the described external disinfection of the external surface of the plastics material pre-forms 10. This can be carried out by a nozzle ring which is arranged above the aperture of the plastics material pre-form and which conveys the sterilization medium to the inner walls of the plastics material pre-forms. The feed of sterilization medium for the internal and external disinfection can be carried out from a central common reservoir.

FIGS. 4*a* to 4*e* show a plurality of illustrations wherein the plastics material pre-forms 10 or the external surfaces thereof are acted upon with the sterilization medium. In the case of the embodiment shown in FIG. 4*a* the stressing device acts both upon the plastics material pre-forms directly as well as a flow deflecting device 16, in which case the sterilization medium bounces off or is reflected and thus arrives at the external surface 10*a* of the plastics material pre-forms indirectly.

Figure 4A:
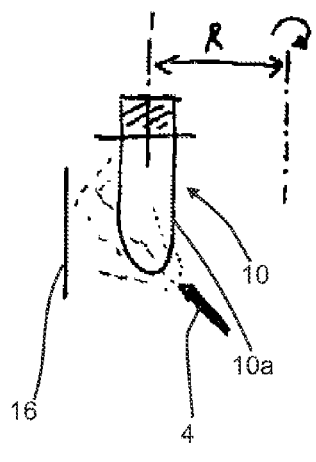
FIGS. 4a to 4e are five illustrations to explain a stressing of plastics material pre-forms with a sterilization medium.
Figure 4B:
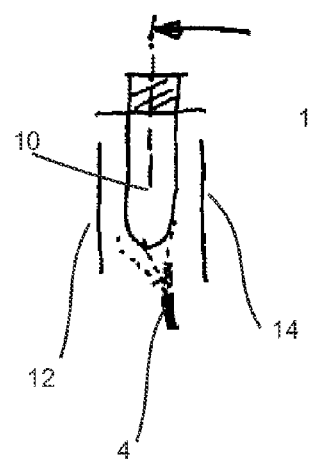

In the case of the embodiment shown in FIG. 4*b* the two walls 12 and 14, between which the plastics material pre-form is conveyed, are again illustrated. In this case it would be additionally possible for the stressing device 4 also to act upon these walls 12 and 14 and for the sterilization medium also to move from these walls indirectly to the plastics material pre-forms or the outer wall thereof respectively.

Figure 4C:
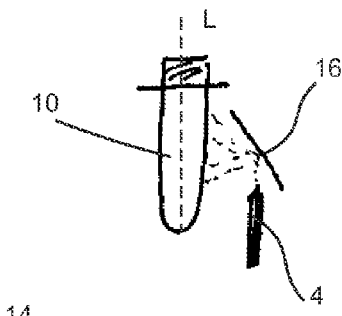

FIG. 4*c* is a further illustration of the stressing. In this case a deflecting device 16 is provided which is arranged obliquely with respect to the longitudinal direction L of the plastics material pre-forms 10 and which is acted upon by the stressing device 4 and, in this way, acts in turn upon the plastics material pre-forms 10 indirectly.

Figure 4D:
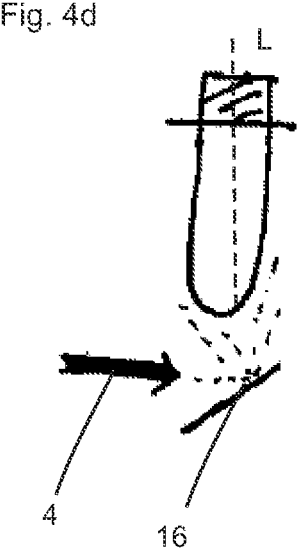

FIG. 4*d* shows a further embodiment of the stressing. In this case both the stressing device 4 and the deflecting device 16 are arranged below the plastics material pre-form and the sterilization medium is reflected by the deflecting device and is projected onto the plastics material pre-form. In addition, it would also be possible for rotation devices to be provided which rotate the plastics material pre-forms 10 with respect to their own longitudinal axis L, so that the outer wall of the plastics material pre-forms is acted upon with the sterilization medium as comprehensively as possible. In principle, it would also be possible for at least one deflecting device 16 or a stressing device 4 to be arranged in a region between an axis of rotation of the carrier 2 and a longitudinal axis of the plastics material pre-form 10 which is held by the holding devices 22.

Figure 4E:
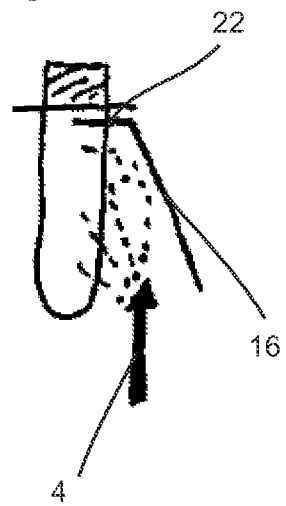

In the case of the embodiment shown in FIG. 4*e* the deflecting device 16 is arranged so as to be movable with the stressing devices 4, i.e. it moves with the latter. In addition, a holding means for holding the plastics material pre-forms can also be arranged on the deflecting device 16 in this case.

Figure 5:
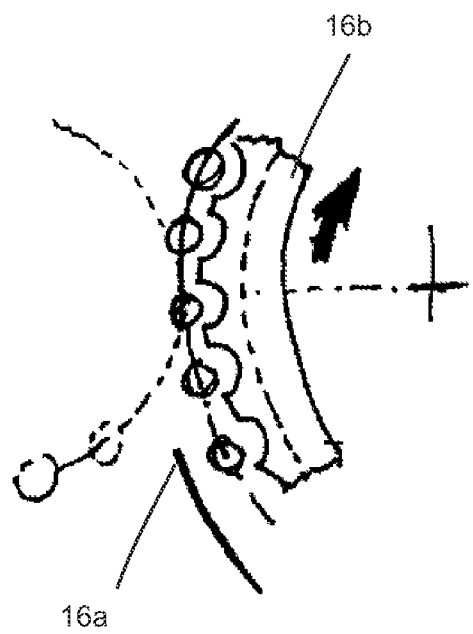
FIG. 5 is a further illustration of the invention in a transfer region.

FIG. 5 is an illustration to explain the transfer of the plastics material pre-forms. In this case there are provided both a first stationary deflecting device 16*a* and a movable deflecting device 16*b* which in this case also forms holding means for the plastics material pre-forms at the same time. This means that in this case both the deflecting device 16*a* and the deflecting device 16*b* contribute to the improved stressing of the plastics material pre-forms 10 with the sterilization medium.

The Applicants reserve the right to claim all the features disclosed in the application documents as being essential to the invention, insofar as they are novel either individually or in combination as compared with the prior art.

LIST OF REFERENCES 1 apparatus according to the invention
2 rotatable carrier
4 stressing devices
6 flow generation device
10 plastics material pre-forms
10*a* external surface
12, 14 curved walls
16 flow deflecting device, deflecting device
16*a* first deflecting device
16*b* movable deflecting device
20, 30 sterilization units
25 conveying device
22 holding devices
42 annular duct
46 distribution device
48 plurality of lines
T conveying path
L longitudinal axis

The invention claimed is:

1. An apparatus (1) for the sterilization of plastics material containers (10), and in particular of plastics material pre-forms (10), with a conveying device (2) which conveys the plastics material containers (10) along a pre-set conveying path, with at least one stressing device (4) which acts upon an external surface of the plastics material containers to be sterilized with a flowable medium, wherein the stressing device is arranged in such a way that it acts upon a pre-set area of the plastics material containers (10)—situated below an aperture of the plastics material pre-forms—with the sterilization medium;
wherein the stressing device is arranged below the aperture of the containers in such a way, that sterilizing medium originating from the stressing device is impinging from below onto the outer surface of the container.

2. An apparatus (1) according to claim 1, wherein the stressing device (4) is arranged below the conveying path (T) of the plastics material pre-forms.

3. An apparatus (1) according to claim 1, wherein the stressing devices (4) move jointly with the plastics material pre-forms (10) in the conveying direction of the latter.

4. An apparatus (1) according to claim 3, wherein the apparatus has a second wall (14), wherein the conveying path (T) of the plastics material pre-forms is arranged between the first wall (12) and the second wall (14).

5. An apparatus (1) according to claim 1, wherein the sterilization medium is turbulent in the region of the plastics material pre-forms.

6. An apparatus (1) according to claim 1, wherein the apparatus has a first wall (12) which extends in a direction of the conveying path and which is preferably situated at the side of the conveying path (T).

7. An apparatus (1) according to claim 1, wherein the apparatus (1) has a plurality of stressing devices which are arranged one behind the other along the conveying path (T) of the plastics material containers (10).

8. An apparatus (1) according to claim 1, wherein the apparatus (1) has a flow generation device (6) which generates a flow of the flowable medium in the region of the conveying path.

9. An apparatus (1) according to claim 1, wherein the apparatus has a deflecting device which deflects a flow of the flowable sterilization medium.

10. An apparatus (1) according to claim 9, wherein the deflecting device is arranged obliquely with respect to the longitudinal direction (L) of the plastics material pre-forms (10) and is acted upon by the stressing device (4) and, in this way, acts in turn upon the plastics material pre-forms (10) indirectly.

11. An apparatus (1) according to claim 1, wherein the apparatus has a further sterilization device which sterilizes an internal surface of the plastics material pre-forms.

12. A method of sterilization of plastics material pre-forms (10), wherein the plastics material pre-forms (10) are conveyed along a pre-set conveying path (T) and at least one region of an external surface (10*a*) of the plastics material pre-form (10) is acted upon with a flowable sterilization medium during this conveying, wherein at least one region of the external surface of the plastics material pre-forms, which is situated below an aperture region of the plastics material pre-forms (10), is acted upon by at least one stressing device (4).

13. A method according to claim 12, wherein a flow of the sterilization medium is actively generated in a surrounding region of the plastics material pre-forms (10).

14. A method according to claim 12, wherein the flow of the sterilization medium is turbulent.

15. A method according to claim 12, wherein the plastics material pre-forms are conveyed during the sterilization thereof through a conveying channel which surrounds the conveying path (T) of the plastics material pre-forms at least locally.

16. A method according to claim 12, wherein an internal surface of the plastics material pre-forms is also sterilized, wherein the external sterilization of the plastics material pre-forms and the internal sterilization of the plastics material pre-forms is preferably carried out at the same time at least in part.

17. A method according to claim 12, wherein the stressing device acts both upon the plastics material pre-forms directly as well as a deflecting device, in which case the sterilization medium bounces off or is reflected and thus arrives at the external surface (10*a*) of the plastics material pre-forms indirectly.

18. An apparatus (1) for the sterilization of plastics material containers (10), and in particular of plastics material pre-forms (10), with a conveying device (2) which conveys the plastics material containers (10) along a pre-set conveying path, with at least one stressing device (4) which acts upon an external surface of the plastics material containers to be sterilized with a flowable medium, wherein the stressing device is arranged in such a way that it acts upon a pre-set area of the plastics material containers (10)—situated below an aperture of the plastics material pre-forms—with the sterilization medium;

wherein the stressing device (4) is arranged below the conveying path (T) of the plastics material pre-forms;

wherein the stressing devices (4) move jointly with the plastics material pre-forms (10) in the conveying direction of the latter; and wherein a plurality of stressing devices are arranged on a common ring.

\* \* \* \* \*